United States Patent
Mumford et al.

(10) Patent No.: US 7,283,866 B2
(45) Date of Patent: Oct. 16, 2007

(54) NEEDLE HAVING MULTIPLE ELECTRODES

(75) Inventors: John Robert Mumford, Mississauga (CA); Ronald Leon Kurtz, Oakville (CA)

(73) Assignee: Hatch Ltd, Oakville (CA)

( * ) Notice: Subject to any disclaimer, the term of this patent is extended or adjusted under 35 U.S.C. 154(b) by 0 days.

(21) Appl. No.: 11/130,222

(22) Filed: May 17, 2005

(65) Prior Publication Data

US 2005/0261602 A1    Nov. 24, 2005

Related U.S. Application Data

(60) Provisional application No. 60/571,944, filed on May 18, 2004, provisional application No. 60/571,890, filed on May 18, 2004, provisional application No. 60/571,942, filed on May 18, 2004.

(51) Int. Cl.
   *A61B 5/04*    (2006.01)
(52) U.S. Cl. ............................................ 600/546
(58) Field of Classification Search ............... 600/547, 600/374, 407, 585; 604/274, 280; 606/41
   See application file for complete search history.

(56) References Cited

U.S. PATENT DOCUMENTS

| | | | |
|---|---|---|---|
| 3,313,293 A | 4/1967 | Chesebrough et al. | |
| 3,682,162 A | 8/1972 | Colyer | |
| 4,082,087 A | 4/1978 | Howson | |
| 4,561,445 A | 12/1985 | Berke et al. | |
| 5,058,602 A | * 10/1991 | Brody | 600/546 |
| 5,161,533 A | 11/1992 | Prass et al. | |
| 5,223,124 A | * 6/1993 | Ege | 204/403.09 |
| 5,306,236 A | 4/1994 | Blumenfeld et al. | |
| 5,497,781 A | 3/1996 | Chen et al. | |
| 5,579,781 A | 12/1996 | Cooke | |
| 5,830,151 A | 11/1998 | Hadzic et al. | |
| 5,916,172 A | 6/1999 | Hodges et al. | |
| 6,292,701 B1 | 9/2001 | Prass et al. | |
| 6,306,100 B1 | 10/2001 | Prass | |
| 6,334,068 B1 | 12/2001 | Hacker | |
| 6,411,842 B1 | 6/2002 | Cigaina et al. | |
| 6,466,817 B1 | 10/2002 | Kaula et al. | |

(Continued)

OTHER PUBLICATIONS

Jun Kimura, "Electrodiagnosis in Diseases of Nerve and Muscle: Principles and Practice", F.A. Davis Company, 2nd edition, pp. 38-41.

(Continued)

*Primary Examiner*—Max Hindenburg
*Assistant Examiner*—Fangemonique Smith
(74) *Attorney, Agent, or Firm*—Bereskin & Parr; Sylvan S. Browne

(57) ABSTRACT

Embodiments of the invention generally relate to needles having more than one electrode and which are particularly suited for use in electromyography. One embodiment relates to a tripolar needle having three concentric electrodes. The tripolar needle is formed by providing a needle blank having first and second concentric electrodes and forming a third concentric electrode around the needle blank. The tripolar needle has an outer diameter which is substantially constant along the shaft of the needle, except at the tip, where the needle is sharpened.

36 Claims, 8 Drawing Sheets

U.S. PATENT DOCUMENTS

| | | |
|---|---|---|
| 6,500,128 B2 | 12/2002 | Marino |
| 6,649,605 B2 * | 11/2003 | Olesen et al. ................ 514/215 |
| 6,678,550 B2 | 1/2004 | Hubbard, Jr. |
| 6,922,579 B2 * | 7/2005 | Taimisto et al. ............ 600/374 |
| 6,936,006 B2 * | 8/2005 | Sabra ......................... 600/300 |
| 2004/0024439 A1 | 2/2004 | Riso |

OTHER PUBLICATIONS

Jun Kimura, "Electrodiagnosis in Diseases of Nerve and Muscle: Principles and Practice", Oxford University Press, 3rd edition, 2001, pp. 38-41.

* cited by examiner

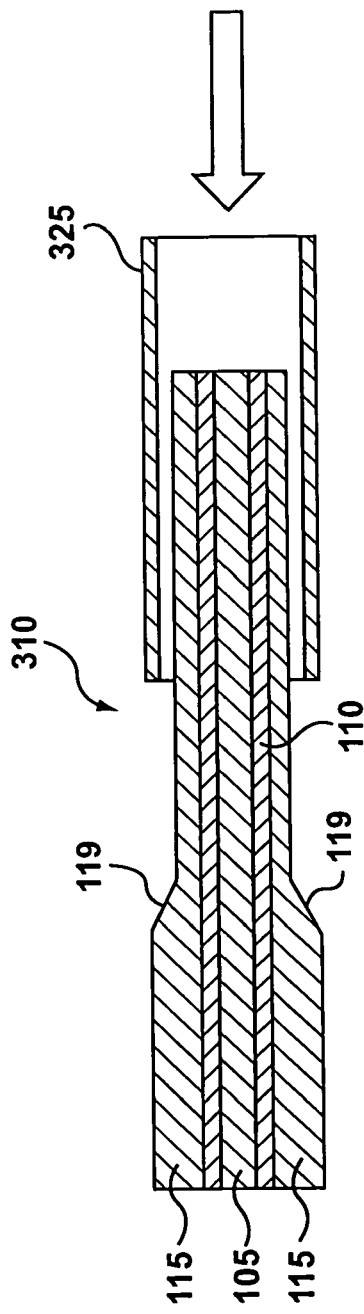
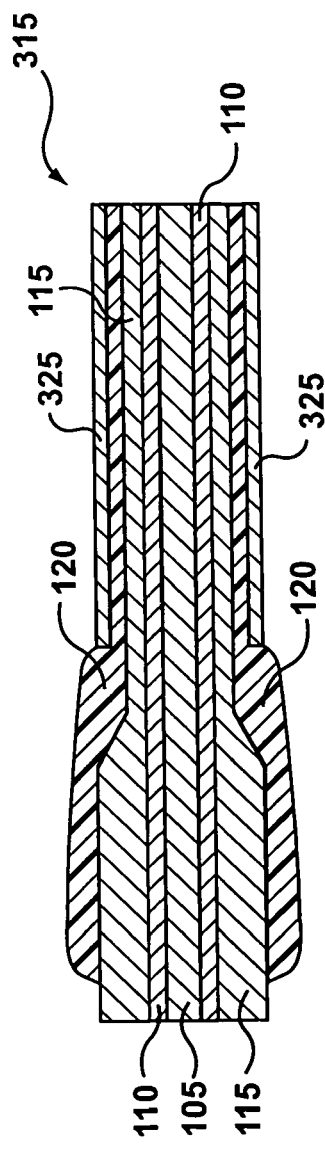
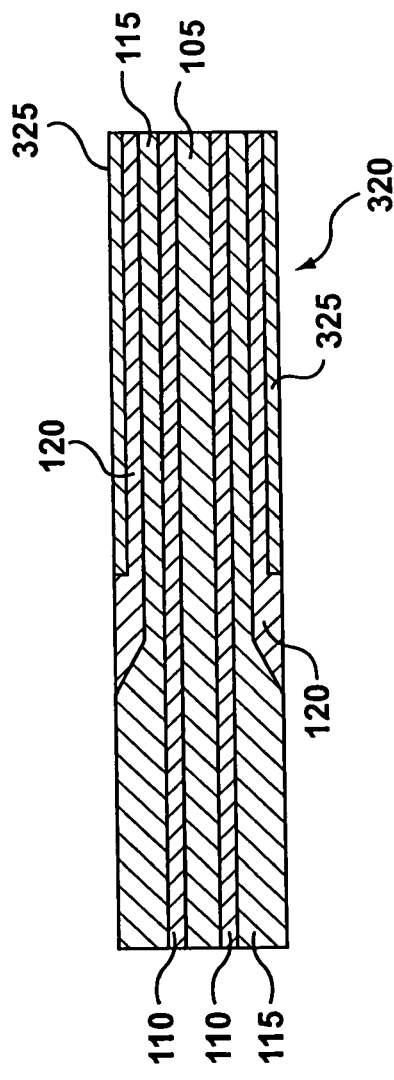
FIG. 3A
FIG. 3B
FIG. 3C

NEEDLE HAVING MULTIPLE ELECTRODES

RELATED APPLICATIONS

This application claims the benefit of from U.S. Provisional Application Ser. No. 60/571,944 filed on May 18, 2004, the entire contents of which are hereby incorporated by reference, U.S. Provisional Patent Application Ser. No. 60/571,890, filed on May 18, 2004, the entire contents of which are hereby incorporated by reference and U.S. Provisional Patent Application Ser. No. 60/571,942 filed on May 18, 2004, the entire contents of which is hereby incorporated by reference.

FIELD OF THE INVENTION

The present invention relates to needles having multiple electrodes. In particular, the invention relates to needles having bipolar and tripolar electrode arrangements which may be used in electromyography.

BACKGROUND OF THE INVENTION

Needles are frequently used in electromyography (EMG) for detecting electrical signals within the body. Commonly, needles used in electromyography have one or two electrodes, termed monopolar and bipolar, respectively.

If the diameter of a needle is too large, it can cause significant pain to the person in whom it is inserted. Thus it is desirable to have as small a diameter as possible.

For needles having bipolar electrodes, one of the electrodes is usually a reference conductor while the other is used as an active conductor. A common or ground conductor is placed on the skin externally of the point at which the body's electrical activity is being monitored. This placement of the common conductor on the skin takes time during the EMG set up procedure. Further, the signal quality achieved with a common electrode remote from the measurement point of the active and reference electrodes is sub-optimal.

Some needles use a beveled tip. That is, the needle tip is cut at an angle from one side to the other, presenting a substantially elliptical face in the plane of the cut (assuming that the needle is of circular cross-section). Because of the elliptical shapes of the electrodes exposed on the elliptical face, the distance between the central electrode and the outer concentric electrode is not uniform across the exposed elliptical face of the needle at its tip. This lack of uniformity of distance between the two electrodes can lead to inaccuracies in the signal detection.

A further problem with existing beveled tip concentric needles is that when they are constructed with a small outer diameter, the gap between the active and reference electrodes is often quite small, leading to lower amplitude signals and smaller effective measurement area. There is also a tendency for the electrodes to short circuit after the tip becomes worn by repeated insertions. Also, the area of the exposed surface of the inner conductor is small, resulting in low signal amplitudes.

SUMMARY OF THE INVENTION

In one aspect, the invention relates to a needle for electromyography having a distal sharpened tip portion and a shaft, the needle comprising:

first, second and third concentrically arranged electrodes for acting as respective active, reference and ground conductors during electromyography; and first and second insulation layers for separating the first and second electrodes and the second and third electrodes, respectively;

wherein the third electrode at least partly defines an outer diameter of the shaft and the shaft has a substantially constant outer diameter proximally of the distal top portion.

Preferably, the needle is formed from a needle blank having first and second concentric electrodes. An outer insulation layer is formed around the needle blank and a third electrode is formed around the outer insulation layer.

The third electrode is preferably exposed at least to some extent along a shaft portion of the needle. The first and second concentric electrodes are preferably exposed at least to some extent along a tip portion of the needle.

In a preferred embodiment, the outer diameter of the needle is in the range 0.3 mm to 0.65 mm. The needle is preferably formed so that an outer diameter of the third electrode is substantially the same as an outermost diameter of the needle blank, which is substantially the same as an outermost diameter of the needle.

In a further aspect, the invention relates to a method of forming a needle, comprising providing a needle blank having first and second concentric electrodes and an outer insulation layer and forming a third concentric electrode around the needle blank.

In a still further aspect, the invention relates to a method of forming a needle, comprising providing a needle blank having first and second concentric electrodes, forming an outer insulation layer around the needle blank and forming a third concentric electrode around the outer insulation layer.

According to these method aspects, it is preferred that the third electrode is formed along a shaft portion of the needle, away from a tip portion of the needle. Further, it is preferred that the needle is formed so that an outer diameter of the third electrode is substantially the same as an outermost diameter of the needle blank, which is substantially the same as an outermost diameter of the needle.

In yet another aspect, the invention relates to a method of forming a needle, comprising the steps of: providing a needle blank having first and second concentric electrodes, the first electrode being formed inwardly of the second electrode; removing a portion of the second electrode along a shaft of the needle; adding an insulation layer around the needle at least along the part of the shaft from which the portion of the second electrode was removed; providing a conductor layer around the insulation layer; and cutting excess added insulation material from the needle so that the outer diameter of the needle is the same as the outer diameter of the needle blank whereby a third concentric electrode is formed from the conductor layer at least partly along the portion of the shaft from which the portion of the second electrode was removed.

In yet another aspect, the invention relates to a method of forming a needle, comprising providing a needle blank having first and second electrodes, providing an insulation material around at least part of the needle blank and providing a conductive material around at least part of the insulation material to form a third electrode.

In one embodiment, the conductive material comprises a conductive sheath, which is preferably in the form of a metallic tube. In another embodiment, the conductive material is plated or coated on the outside of the insulation material.

Preferably, the method includes removing a portion of the needle blank before providing the insulation material. The portion removed from the needle blank is preferably substantially tubular or sheath like. Preferably, the first, second and third electrodes are concentrically arranged. Preferably, the first electrode is an active conductor and is disposed inwardly of the second electrode, the second electrode is a reference conductor and is disposed inwardly of the third conductor and the third electrode is a common or ground conductor.

In a preferred embodiment of the method, one end of the needle blank is sharpened so as to provide a substantially conical or frustoconical shape thereto. Alternatively, the needle blank may have one end sharpened so as to provide a beveled tip shape thereto.

Preferably, the needle is formed so as to have an outer diameter along a shaft thereof substantially the same as an outermost diameter of the needle blank.

In a still further aspect, the invention relates to a method of forming a needle, comprising providing a needle blank having first and second concentric electrodes, providing a conductive material around at least part of the needle blank and injecting an insulating material between the needle blank and the conductive material.

In another aspect, the invention relates to a needle for electromyography having first and second electrodes and a sharpened tip, wherein the first and second electrodes are exposed on said tip such that the first and second electrodes are separated by a constant gap.

The tip is preferably sharpened so as to have a substantially conical or frustoconical shape. The first and second electrodes are preferably concentrically arranged. The first electrode extends along a central longitudinal axis of the needle. The first and second electrodes are separated by a concentrically arranged insulation layer and the second electrode defines an outer diameter of the needle.

In a further aspect, the invention relates to a method of forming a needle, comprising providing a needle blank having first and second electrodes and sharpening one end of the needle blank so as to form a sharpened tip and so that the first and second electrodes are exposed on said tip such that exposed potions thereof are separated by a constant gap.

Preferably, the method includes sharpening the tip so as to have a substantially conical or frustoconical shape. Preferably, the first and second electrodes are concentrically arranged and are separated by a concentric insulation layer.

BRIEF DESCRIPTION OF THE DRAWINGS

Embodiments of the invention will be described in further detail, by way of example only, with reference to the accompanying drawings, in which:

FIGS. 3A to 3C are side cross-sectional illustrations of alternative method steps for forming a tripolar concentric needle.

Figure 1:
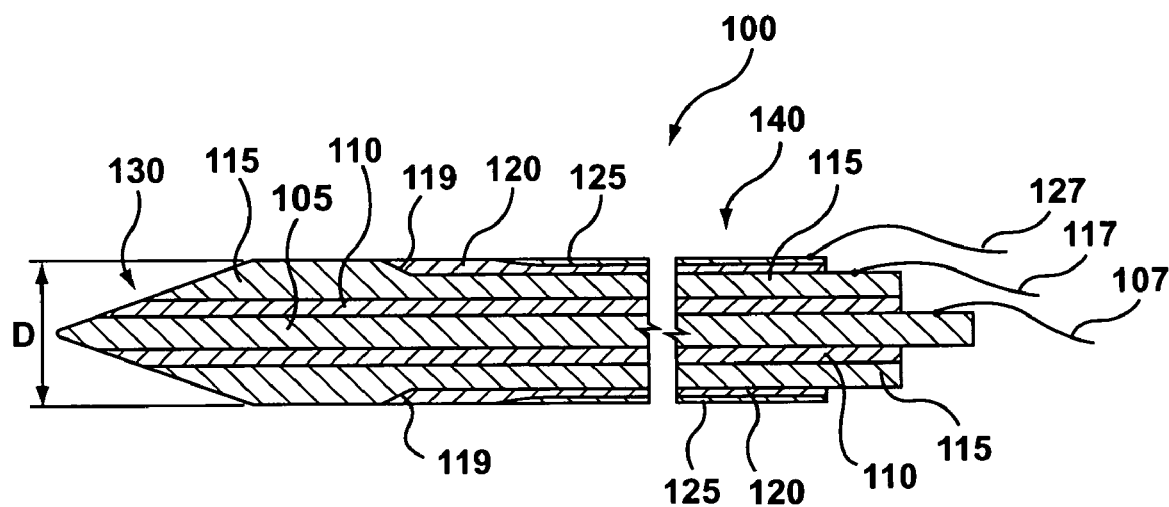
FIG. 1 is a side cross-sectional view of a tripolar concentric needle according to an embodiment of the invention.

The drawings are not to scale.

DETAILED DESCRIPTION OF THE INVENTION

Embodiments of the invention generally relate to needles having more than one electrode and which are particularly suited to use in electromyography (EMG). Such embodiments of the invention relate to methods of forming such needles.

Throughout the following description, like reference numerals are used to indicate like components, features or functions. It should be understood that features, components or functions described in relation to one embodiment may also be employed in relation to any other embodiment, except where it would be apparent to those skilled in the art that such a combination would be unworkable.

The term "proximate" and "proximal" will be used herein to indicate a direction away from the needle tip. The term "distal" will be used herein to indicate a direction toward, or in the vicinity of, the needle tip.

Referring now to FIG. 1, there is shown a side (longitudinal) cross-sectional cylindrical tripolar needle 100. Needle 100 is called tripolar because it has three conductors, namely a central conductor 105, a cannula 115 and an outer conductor 125. Central conductor 105, cannula 115 and outer conductor 125 are electrically connected to an end cap (not shown) engaging a proximal end of the needle 100. In one embodiment, the electrical connections are made by respective electrical contacts 107, 117 and 127 by means of an interference fit with respective contacts in the end cap. Although FIG. 1 indicates that electrical contacts 107, 117 and 127 are made by wire connection, this is less preferred than connection by interference fit.

Central conductor 105 is connected by a wire connection 107 so as to be the active electrode, while cannula 115 is connected via wire connection 117 so as to be the reference electrode. Outer conductor 125 is connected via wire connection 127 so as to be a common or ground electrode.

Central conductor 105 is separated from cannula 115 by an inner insulator 110 surrounding the central conductor 105 in a cylindrical manner. Cannula 115 is substantially cylindrical and is concentric with central conductor 105 and inner insulator 110. Outer insulator 120 is overlayed on cannula 115, at least along shaft 140 of the needle away from tip 130. Outer conductor 125 substantially cylindrical and is overlayed on outer insulator 120 and concentric therewith, while also being concentric with cannula 115 and central conductor 105.

Needle 100 has an outer diameter D which is constant along the shaft 140. At tip 130, which is substantially conically or frustoconically shaped, the diameter of needle 100 focuses toward a point, although due to physical limitations, the extremity of tip 130 can never truly be formed as a point. At tip 130, central conductor 105, inner insulator 110 and cannula 115 have exposed frustoconical portions for contact with a desired part of anatomy during EMG. At tip 130 and along the outer diameter of needle 100 proximally adjacent tip 130, cannula 115 is the outermost exposed electrode. More proximally of tip 130, cannula 115 reduces in diameter (via a short frustoconical ramp 119) and outer conductor 125 becomes the outermost exposed electrode. Outer insulator 120 completely separates cannula 115 from outer conductor 125 at all points along shaft 140 and tip 130.

Although not shown in the drawings, needle 100 (and other needle embodiments described herein) has a substantially circular lateral cross-section.

The outer diameter of needle 100 ranges from 0.3 mm to 0.65 mm. Larger diameter needles are suited for deep anatomical structures or muscles with large motor units. Small diameter needles are more suited for muscles near the surface with small motor units, such as muscles in the hands and face.

The central conductor 105 is formed of a wire core having a diameter in the range of 0.025 mm to 0.1 mm. The wire core is formed of platinum, platinum-iridium or other biocompatible metals or alloys.

Cannula 115 has an outermost diameter of 0.3 mm to 0.65 mm and a thickness in the range of 0.1 mm to 0.45 mm. The cannula 115 is formed of stainless steel (series 303, 304, 316 or 400), platinum, platinum-iridium, silver or other biocompatible conductive metals or alloys. Cannula 115 may also be plated in gold or gold alloy. An intermediate diameter of cannula 115 (i.e. where the cylindrical portion has been removed) is in the range of 0.2 mm to 0.55 mm.

Outer conductor 125 has an outer diameter in the range of 0.3 mm to 0.65 mm, which is the same as cannula 115. The radial thickness of outer conductor 125 is in the range of 0.25 µm to 0.4 mm. Outer conductor 125 may be formed from stainless steel (series 303, 304, 316 or 400), platinum, platinum-iridium, silver or other biocompatible conductive metals or alloys. Outer conductor 125 may also be plated in gold or gold alloy.

Inner insulator 110, also called a core insulator, is preferably made from epoxy, Teflon or other non-conductive biocompatible materials. The radial thickness of inner insulator 110 is at least 0.075 mm for effective insulation.

Outer insulator 120 is preferably formed of epoxy, Teflon or other non-conductive biocompatible materials. The radial thickness of the outer insulator 120 is at least 0.075 mm for effective insulation.

Figure 4:
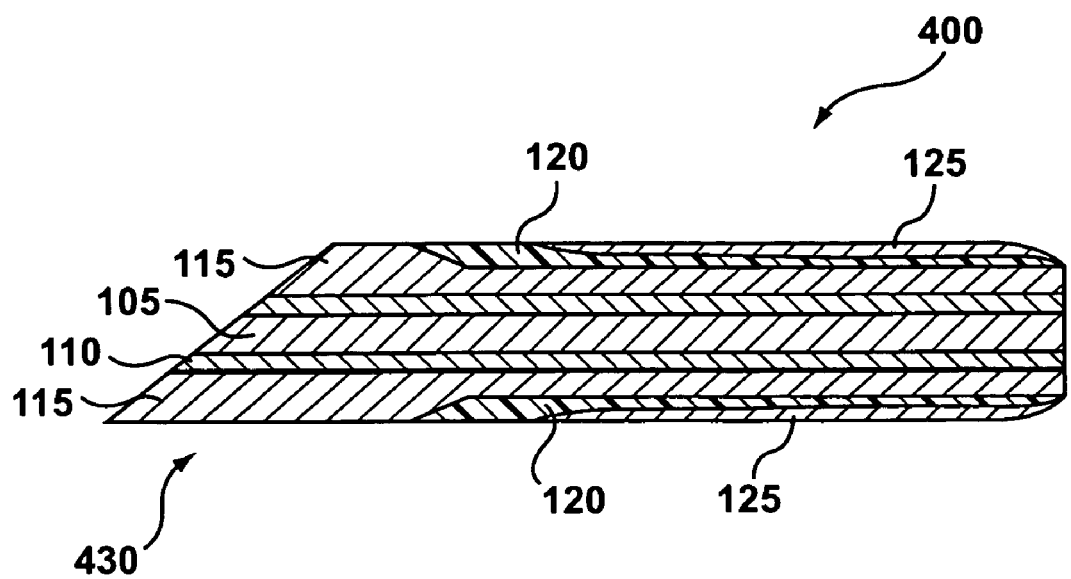
FIG. 4 is a side cross-sectional view of a tripolar concentric needle according to an embodiment of the invention.

Tip 130 of needle 100 may be formed as a pencil tip (i.e. generally conical or frustoconical), such as is shown in FIG. 1, or alternatively as a beveled tip, such as is shown in FIG. 4. The preferred angle of the tip is about 15 degrees, but it may range from about 5 to 25 degrees. The distance from the tip point to the most distal part of the outer conductor 125 is preferably in the range of 0.2 mm to 10 mm.

The outer diameter of cannula 115 adjacent tip 130 is the same as that which would be used for a bipolar electrode needle. Thus, according to a preferred embodiment of the invention, a tripolar electrode needle can be obtained without increasing the diameter of the needle.

Advantageously, tripolar embodiments of the invention allow a common electrode to be located in close proximity to the active and reference electrodes. Further advantageously, the common electrode does not need to be placed on the skin as a separate, time-consuming action because it can be inserted along with the active and reference electrodes as part of the needle.

Thus, tripolar embodiments of the invention can achieve better signal quality by having the common electrode close to the active and reference electrodes, while enabling a more time-efficient EMG set up procedure. This is achieved without increasing the diameter of the needle beyond that of a standard bipolar needle and therefore without increasing the pain inflicted on the patient.

Referring now to FIGS. 2A to 2G, there are shown side cross-sections of a needle blank at a number of steps in the formation of needle 100. These steps are part of a method of forming a tripolar needle according to one preferred embodiment of the invention.

Figure 2A:
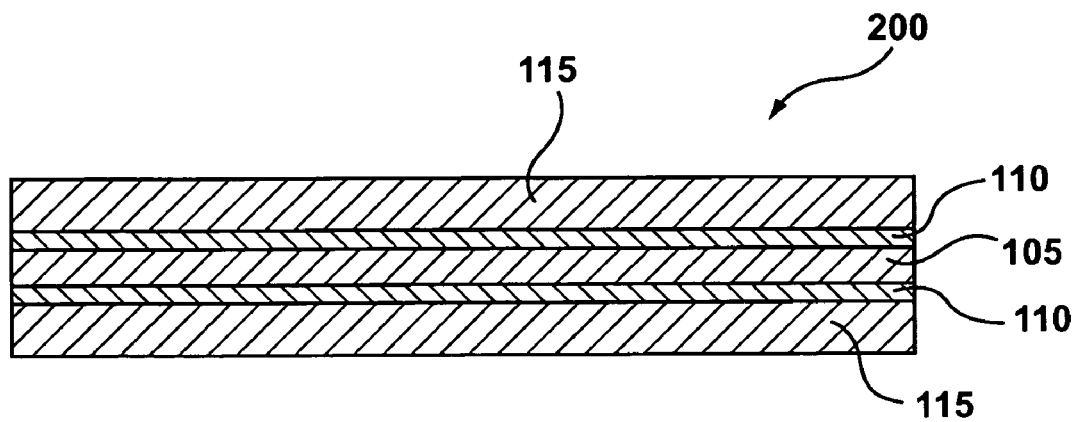
FIGS. 2A to 2G are side cross-sectional illustrations of steps in a method of forming a tripolar concentric needle according to an embodiment of the invention.

Referring first to FIG. 2A, there is shown a needle blank 200, having the cannula 115 concentrically arranged around inner insulator 110 and central conductor 105. Concentric needle blanks such as needle blank 200 are commercially available, for example from Excel-tech Ltd. Of Oakville, Ontario, Canada.

Figure 2B:
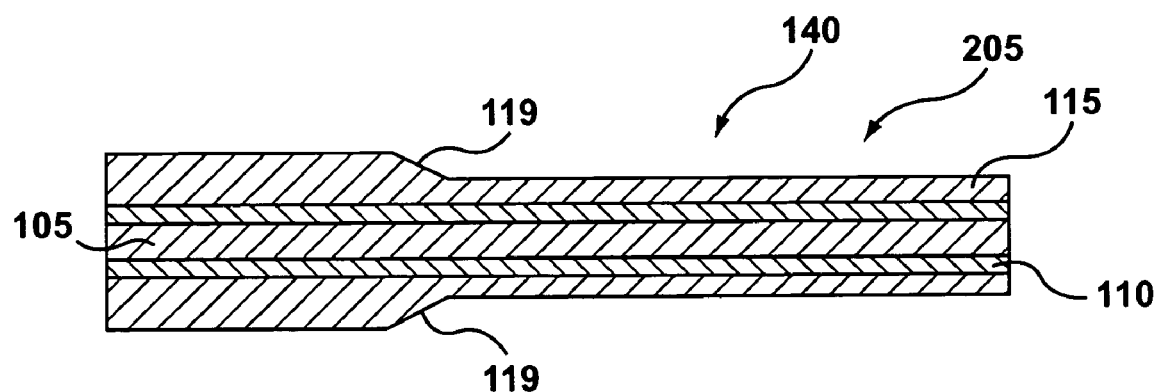

In FIG. 2B, a generally cylindrical portion of the cannula 115 is removed along shaft 140. The needle blank with the cylindrical portion removed is designated by reference numeral 205. A minimum radial thickness of about 75.25 µm is removed from the cannula 115, which is the minimum thickness of the outer insulator 120 and outer conductor 125 combined. The generally cylindrical cannula portion is removed so as to leave a generally frustoconical ramp 119 between the portion of the cannula having been reduced in diameter and the portion of the cannula maintaining its original diameter. The generally cylindrical portion is cut away removed by, for example, etching, grinding or another machining process of suitable precision.

Figure 2C:
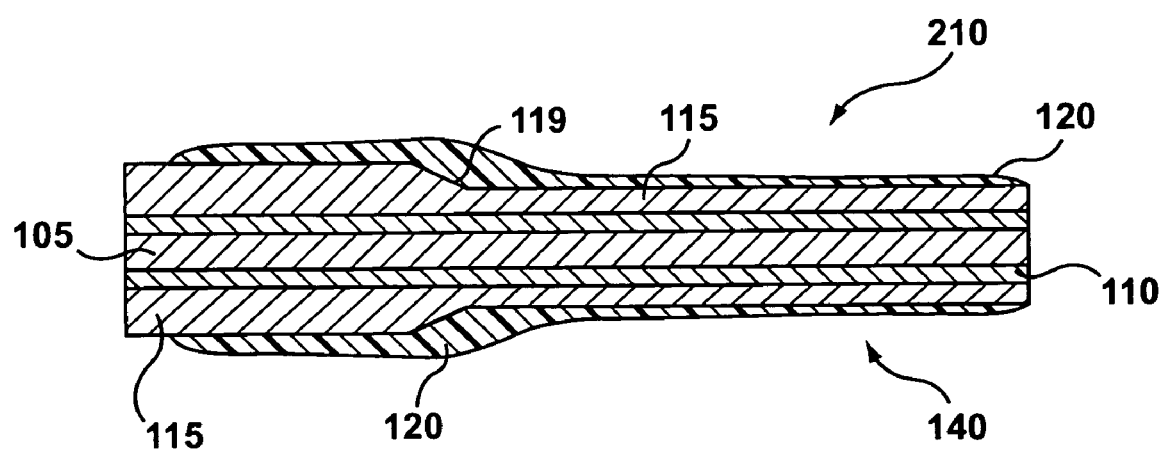

In FIG. 2C, the needle blank is shown with an added insulation layer to form outer insulator layer 120. This form of the needle blank is designated by reference numeral 210. Outer insulator 120 is coated onto needle blank 205 so as to cover substantially the whole length thereof. Along shaft 140, the outer insulator 120 is preferably formed around the outside of cannula 115 so as to have a substantially constant radial thickness less than the outermost diameter of the cannula 115. This allows outer conductor 125 to be formed around outer insulator 120 so as to have an outer diameter not greater than that of the outermost diameter of cannula 115.

Outer insulator 120 is formed by a suitable coating procedure and is allowed to set or cure after it is formed. As an optional step, in order to ensure that the outer insulator 120 is of constant diameter along shaft 140, needle blank 210 may be machined so as to cut away any excess insulator material along shaft 140.

Outer insulator 120 is formed so as to cover ramp 119. Outer insulator 120 is therefore formed more thickly adjacent ramp 119 and immediately proximally thereof. Outer insulator 120 adjacent ramp 119 serves to separate cannula 115 at its outermost diameter from outer conductor 125 along the outside of needle 100.

Figure 2D:
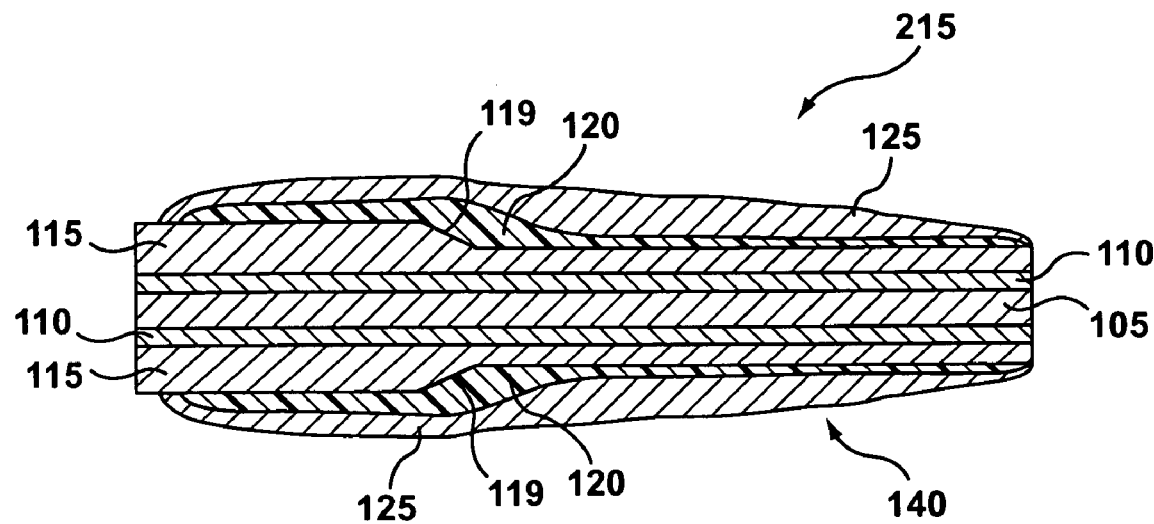

In FIG. 2D, outer conductor 125 is applied to needle blank 210, resulting in a form of the needle blank designated by reference 215. Outer conductor 125 is formed by coating, plating, depositing or other suitable method of forming a layer of conducted material around insulation material.

Outer conductor 125 may be formed around outer insulator 120 with greater thickness than necessary, as any excess material can be cut away. The radial thickness of the outer conductor 125 formed along shaft 140 must be sufficient to bring the outer diameter of outer conductor 125 out to the same diameter as the outermost diameter of cannula 115.

Figure 2E:
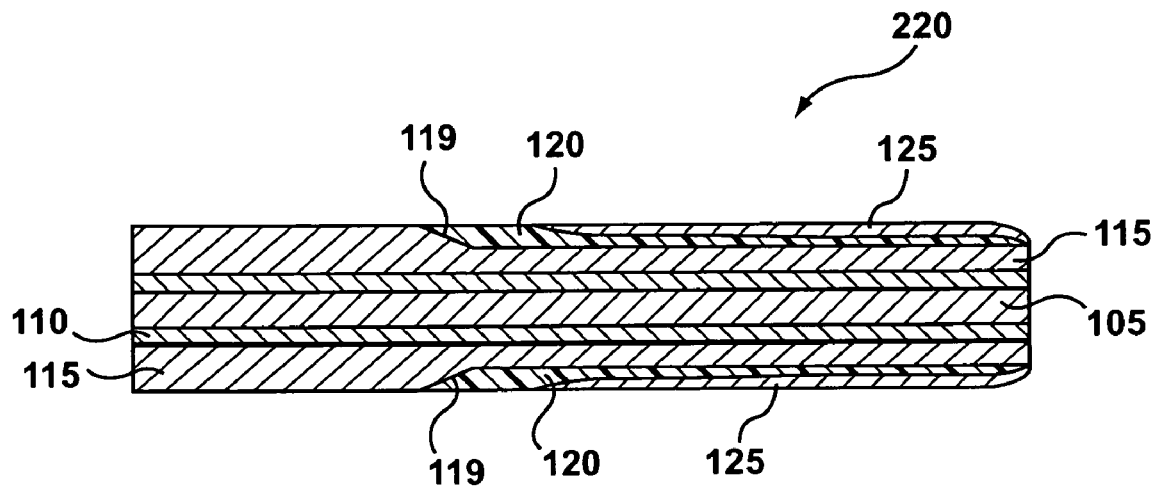

In FIG. 2E, needle blank 215 is cut, machined, etched or otherwise reduced in diameter so as to have a substantially uniform outer diameter along the length of the needle blank, designated by reference numeral 220. In this way, excess conductive and insulative material formed at 210 and 215 are removed so as to leave an outer conductor 125 of substantially constant radial thickness along the length of shaft 140 and separated from cannula 115 by outer insulator 120. Optionally, if sufficient thickness of cannula 115 and outer conductor 125 permit, the outer diameter along the shaft and toward the tip (including the outermost radial part of cannula 115) may be reduced during this cutting step by a thickness of, for example, 0.01 mm to 0.1 mm.

Figure 2F:
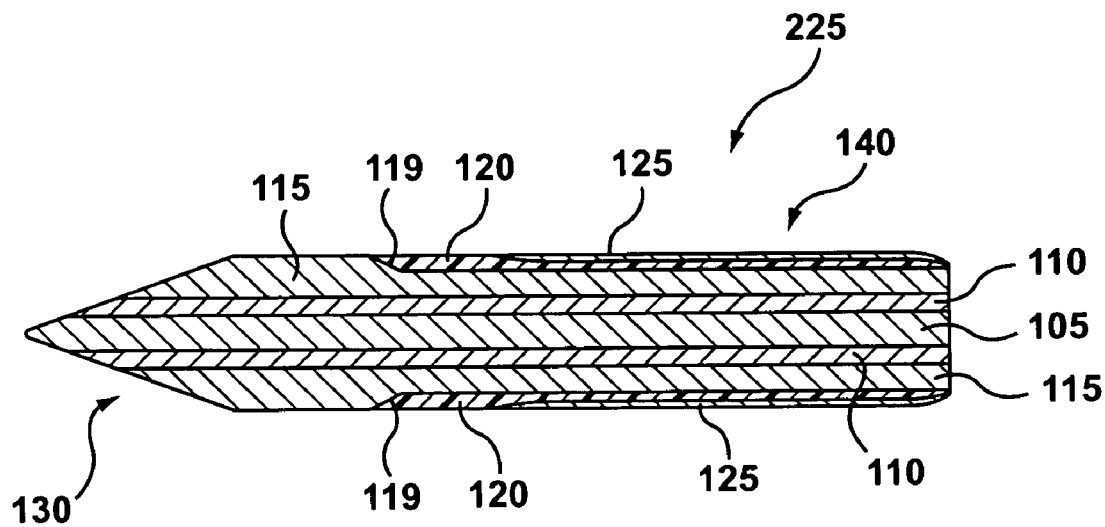

In FIG. 2F, tip 130 is formed so as to enable better penetration of the skin, producing a needle blank designated by reference numeral 225. The tip 130 may be formed by a suitable sharpening method, such as cutting or grinding, so as to provide a tip having an acute angle of between 5 and 25 degrees, and more preferably 15 degrees. Tip 130 is preferably formed so as to be substantially conical or frustoconical, thus resembling a pencil tip, but may be alternatively formed so as to have a beveled edge (see FIG. 4, for example).

According to one embodiment, only central conductor 105, inner insulator 110 and cannula 115 are exposed at tip 130. In an alternative embodiment, tip 130 may be cut so as to also expose outer insulator 120 and outer conductor 125 as part of the tip, rather than only along shaft 140.

Figure 2G:
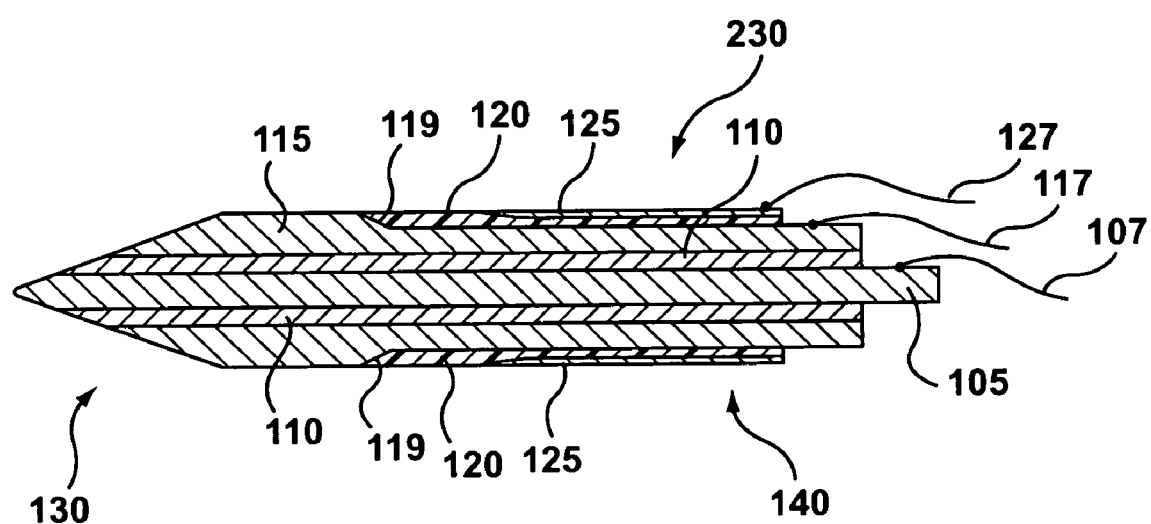

In FIG. 2G, the needle blank formed at 225 is cut or ground at its proximal end so as to expose central conductor 105 and cannula 115. Electrical connections 107, 117 and 127 are formed between central conductor 105, cannula 115 and outer conductor 125, respectively, and the end cap. The end cap preferably forms the electrical connections 107, 117 and 127 by forming a mechanical interference fit with spring-loaded contacts within the end cap. The end cap can then be used to convey electrical signals picked up by the electrodes in the needle to the EMG equipment. The needle shown in FIG. 2G is designated by reference numeral 230, which corresponds to the final step in forming needle 100.

In an alternative method of forming needle 100, needle blank designated by reference numerals 210, 215 and 220 may be formed according to alternative steps, as described hereinafter in relation to FIGS. 3A to 3C.

With reference now to FIG. 3A, instead of forming outer conductor 125 by coating, plating or depositing, a conductive sleeve 325 may be used to form outer conductor 125. After the portion of cannula 115 is removed, conductive sleeve 325 is placed around the outside of the reduced diameter portion of cannula 115, along the length of shaft 140. Conductive sleeve 325 is positioned so that its distal end is positioned proximally of ramp 119. This form of needle blank is designated by reference numeral 310.

As shown in FIG. 3B, a liquid insulator is injected in between conductive sleeve 325 and cannula 115 of needle blank 310. The liquid insulator is preferably epoxy or Teflon, but may be another form of suitable curable material. The outer insulator 120 thus formed by injection is then allowed to set or cure, which fixes the conductive sleeve 325 in place relative to needle blank 310. This injection and curing step results in a needle blank designated by reference numeral 315.

As shown in relation to FIG. 3C, following the injection of outer insulator material 120 after curing thereof, excess insulator material and part of conductive sleeve 325 are removed, for example by machining it, cutting or etching, and the needle blank is then polished to a desired finish to form needle blank 320. The resulting needle blank 320 is of substantially uniform outer diameter and is analogous to needle blank 220.

As an alternative, rather than injecting the insulator fluid between conductive sleeve 325 and cannula 115, insulation material may be formed around the needle blank according to previously described step 210 and conductive sleeve 325 is then slid into position over the insulation layer while the liquid insulator is sufficiently soft and fluid.

In a further alternative, an outer conductive sleeve may be heated to expand and then placed over a solid insulator and allowed to cool and contract. A final cutting step can be used to reduce the outer diameter and to remove excess material.

As an additional step applicable to the above described methods of forming a needle, prior to final formation of needle 100, it is preferred to polish the needle so as to produce a smooth outer surface.

Referring now to FIG. 4, there is shown a needle 400 of similar construction to needle 100, except that it is formed to have a beveled tip 430. Beveled tip 430 is formed by grinding or cutting, for example. Features and functions of needle 400 are otherwise the same as those described in relation to FIGS. 1, 2A to 2G and 3A to 3C.

Figure 5A:
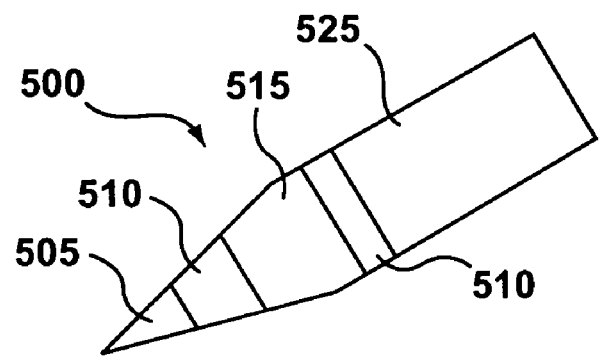
FIGS. 5A and 5B illustrate a tripolar needle in plan and side cross-sectional views, according to another embodiment of the invention.
Figure 5B:
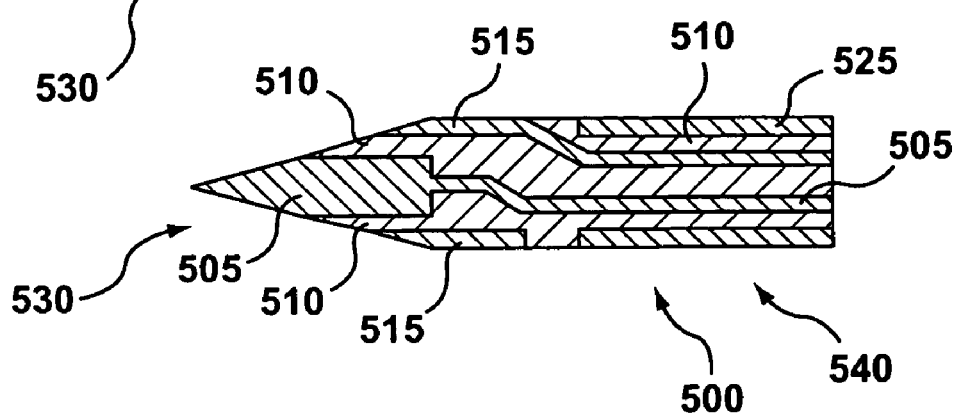

Referring now to FIGS. 5A and 5B, there are shown plan and side cross-sectional views of a further tripolar needle embodiment, designated by reference numeral 500. Needle 500 is substantially similar to needle 100 in form and function, except that it is made with a different internal structure.

Needle 500 comprises a central conductor 505, which acts as an active electrode, an intermediate conductor 515, which acts as a reference electrode, and an outer conductor 525, which acts as a common or ground electrode. Insulator material 510 separates central conductor 505 from the intermediate and outer conductors 515, 525. Outer conductor 525 has an outer diameter which is the same as the outermost diameter of intermediate conductor 515. Outer conductor 525 extends generally proximally of tip portion 530 and intermediate conductor 515.

Central conductor 505, insulator 510 and intermediate conductor 515 are exposed at a pencil tip shaped tip portion 530. Central conductor 505 comprises an enlarged head portion towards tip 530, which is wire bonded to a wire conductor extending within shaft 540 back to a proximal end cap (not shown). Intermediate conductor 515 also has an enlarged head portion at tip 530, extending roughly cylindrically and frustoconically toward the pencil tip shaped end portion 530. Intermediate conductor 515 is also wire bonded to a wire conductor extending proximally along shaft 540 to the end cap.

Figure 6A:
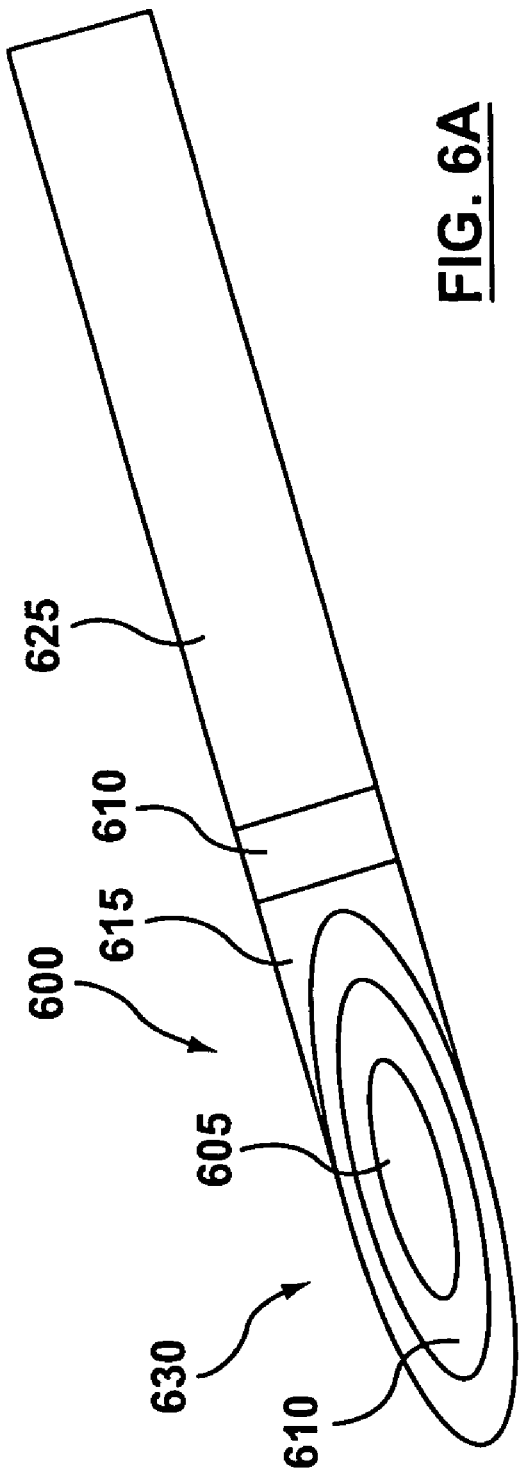
FIGS. 6A and 6B illustrate a tripolar needle in plan side cross-sectional views, according to yet another embodiment of the invention.
Figure 6B:
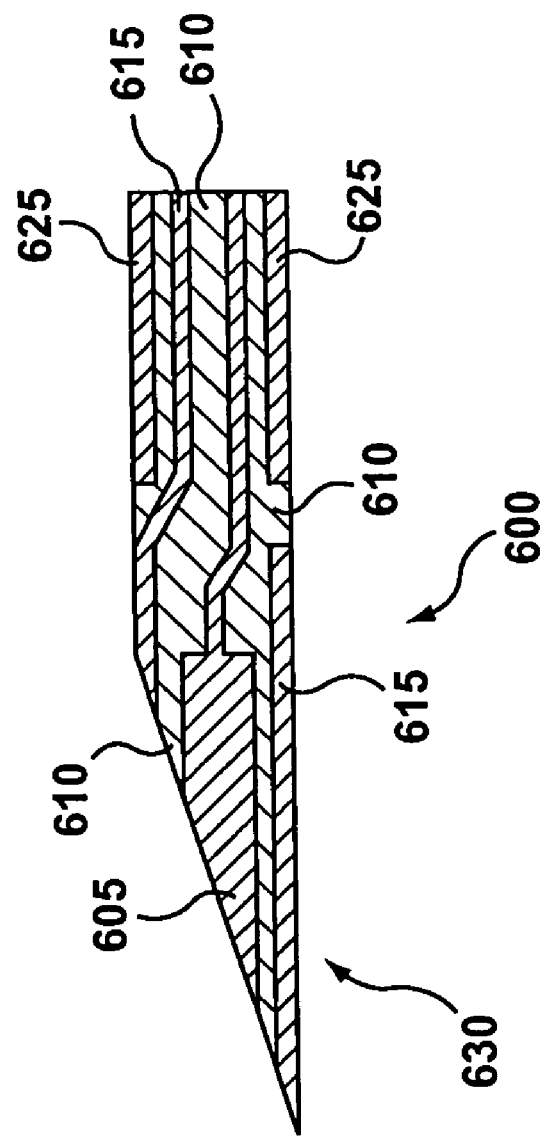

Referring now to FIGS. 6A and 6B, a further tripolar needle embodiment is shown in plan and side cross-section, respectively. Needle 600 is substantially similar to needle 500, except that it has a beveled tip 630 instead of the pencil shaped tip 530. Reference indicators used in relation to FIGS. 6A and 6B correspond generally to those parts shown and described in relation to FIGS. 5A and 5B, where the last two, numbers of the reference numerals are the same. For example, outer conductor 625 corresponds to and has substantially the same form and function of, outer conductor 525.

Figure 7A:
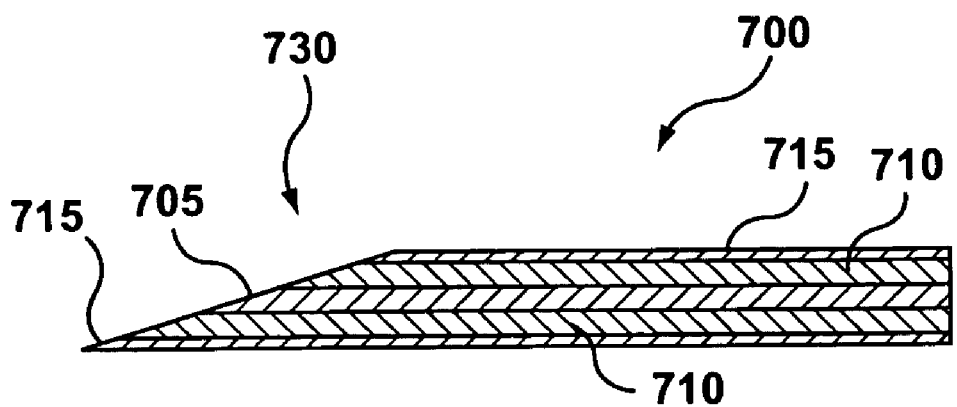
FIGS. 7A and 7B show a bipolar concentric needle having a beveled tip in side cross-section and plan views.
Figure 7B:
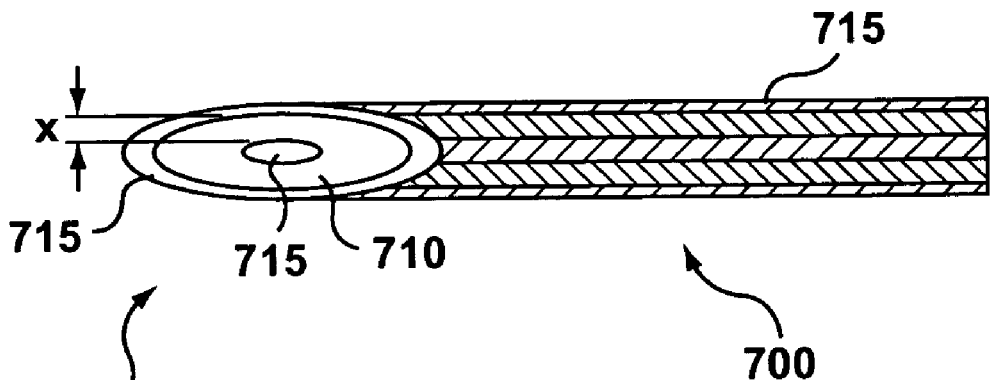

Referring now to FIGS. 7A and 7B, there is shown a concentric bipolar needle 700 having a beveled tip 730. Needle 700 has a central conductor 705 and an outer conductor 715 separated by insulator 710. Needle 700 presents an elliptical face at its tip, where the exposed end surface of central conductor 705 is located in the center of the exposed face. Insulator 710 separates central conductor 705 from outer conductor 715 by a variable distance X according to the position on the exposed elliptical face. The distance X is largest in the direction of longitudinal extension of the needle 700, while it is smallest in the lateral direction, as is evident in FIG. 7B. The exposed elliptical face can be used by a medical practitioner conducting the EMG to directionally target a signal source.

Figure 8:
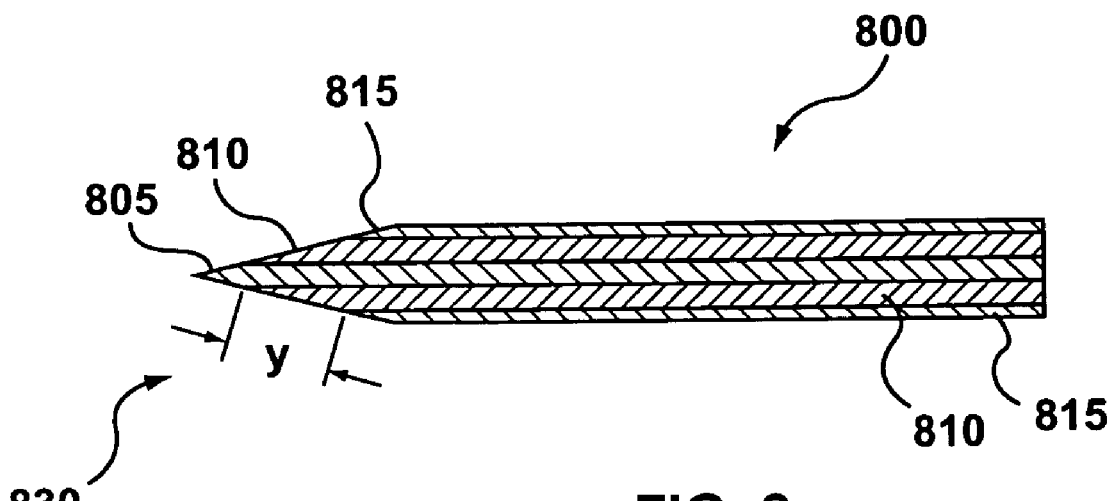
FIG. 8 shows a bipolar concentric needle in side cross-section, according to a further embodiment of the invention.

Referring now to FIG. 8, a further embodiment of the invention is shown in side cross-section as needle 800. Needle 800 has a central conductor 805 and an outer conductor 815 separated by an insulator 810. A tip 830 of needle 800 is formed so as to have the shape of a pencil tip, rather than a beveled tip. Forming the tip 830 of bipolar concentric needle 800 as a pencil tip allows for a distance Y between central conductor 805 and outer conductor 815 to be substantially constant around the tip. The preferred dimensions and materials for needle 800 are the same as for needle 100, where outer diameter 815 equates to cannula 115.

Needle 800 provides a better signal quality than needle 700, resulting from the constant distance between the active and reference electrodes. This distance can be sized to match the typical motor unit being probed, with different tips for different muscles. The constant distance between electrodes also prevents electrical breakdown due to an inadequate insulation gap that can occur with beveled tip geometries.

Needle 800 also provides enhanced patient comfort as the gauge of the needle can be made smaller than conventional concentric needle designs. This is because the same insulation gap as that of a standard beveled tip concentric needle can be achieved with a smaller diameter using a pencil tip. The insulation gap can be further increased by making the angle of the pencil tip more acute, say in the order of 10 degrees.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the invention.

The invention claimed is:

1. An electromyopraphic needle comprising:
a shaft having a distal sharpened tip portion;
first, second and third concentrically arranged electrodes;
first and second insulation layers for separating the first and second electrodes and the second and third electrodes, respectively; and
wherein the shaft has a substantially constant outer diameter proximally of and adjacent to the distal tip portion of the needle and wherein the third electrode is distanced from the distal tip portion and at least partly defines the outer diameter of the shaft proximally of and adjacent to the distal tip portion.

2. The needle of claim 1, wherein the first, second and third electrodes are respective active, reference and ground electrodes during electromyography.

3. The needle of claim 1, wherein the third electrode is at least partially exposed along a substantial length of the shaft.

4. The needle of claim 3, wherein the first and second concentric electrodes are at least partially exposed in the distal tip portion.

5. The needle of claim 4, wherein the distal tip portion is substantially conically shaped.

6. The needle of claim 4, wherein the distal tip portion is substantially frusto-conically shaped.

7. The needle of claim 4, wherein the distal tip portion is beveled.

8. The needle of claim 1, wherein an outer diameter of the needle is between 0.3 millimeters to 0.65 millimeters.

9. The needle of claim 1, wherein the outer diameter of the third electrode is substantially the same as an outer-most diameter of the needle.

10. The needle of claim 1, wherein the first electrode forms a central core of the needle.

11. The needle of claim 10, wherein the first electrode comprises biocompatible material selected from the group consisting of: platinum, platinum-iridium and a platinum alloy.

12. The needle of claim 10, wherein a diameter of the first electrode is between 0.025 millimeters and 0.1 millimeters.

13. The needle of claim 10, wherein an outermost diameter of the second electrode is between 0.3 millimeters to 0.65 millimeters.

14. The needle of claim 10, wherein the second electrode comprises a biocompatible material selected from the group consisting of: stainless steel, platinum, platinum-iridium, silver, platinum alloy, silver alloy, gold and gold alloy.

15. The needle of claim 10, wherein the second electrode has an intermediate outer diameter proximal of the distal tip portion.

16. The needle of claim 15, wherein the intermediate outer diameter is between 0.2 millimeters and 0.55 millimeters.

17. The needle of claim 10, wherein the third electrode has a radial thickness of between 0.25 micrometers and 0.4 millimeters.

18. The needle of claim 10, wherein the third electrode comprises a biocompatible material selected from the group consisting of: stainless steel, platinum, platinum-iridium, silver, platinum alloy, silver alloy, gold and gold alloy.

19. The needle of claim 1, wherein an angle of the distal tip portion relative to a longitudinal axis of the needle is between 5° and 25°.

20. The needle of claim 19, wherein the angle is about 15°.

21. The needle of claim 10, wherein the second electrode has an exposed frustoconical surface at the distal tip portion.

22. The needle of claim 21, wherein the first electrode has an exposed conical or frustoconical surface at the distal tip portion.

23. Use of the needle of claim 1 for electromyography.

24. An electromyoaraphic needle comprising:
a shaft having a sharpened distal tip portion;
first, second and third concentrically arranged electrodes, the first electrode forming a core of the needle at least at the tip portion;
at least one insulation layer separating the first, second and third electrodes; and
wherein the third electrode at least partly defines an outer diameter of the shaft proximally of the distal tip portion and the second electrode has an exposed frustoconical surface at the distal tip portion.

25. The needle of claim 24, wherein the first electrode has an exposed conical or frustoconical surface at the distal tip portion.

26. The needle of claim 24, wherein the distal tip portion is substantially conically or frusto-conically shaped.

27. The needle of claim 24, wherein an outer diameter of the needle is between 0.3 millimeters to 0.65 millimeters.

28. The needle of claim 24, wherein a diameter of the first electrode is between 0.25 millimeters and 0.1 millimeters.

29. The needle of claim 24, wherein an outermost diameter of the second electrode is between 0.3 millimeters and 0.65 millimeters.

30. The needle of claim 24, wherein the second electrode has an intermediate outer diameter proximal of the distal tip portion.

31. The needle of claim 30, wherein the intermediate outer diameter is between 0.2 millimeters and 0.55 millimeters.

32. The needle of claim 24, wherein the third electrode has a radial thickness of between 0.25 micrometers and 0.4 millimeters.

33. The needle of claim 24, wherein the first, second and third electrodes are respective active, reference and ground electrodes during electromyography.

34. The needle of claim 24, wherein an angle of the distal tip portion relative to a longitudinal axis of the needle is between 5° and 25°.

35. The needle of claim 34, wherein the angle is about 15°.

36. Use of the needle of claim 24 for electromyography.

* * * * *